United States Patent
Stradella

(10) Patent No.: US 7,237,549 B2
(45) Date of Patent: Jul. 3, 2007

(54) DEVICE FOR DISTRIBUTING A FLUID OF THE SINGLE DOSE OR HALF DOSE TYPE

(75) Inventor: Guiseppe Stradella, Camogli (IT)

(73) Assignee: Valois S. A. S, Le Neubourg (FR)

( * ) Notice: Subject to any disclaimer, the term of this patent is extended or adjusted under 35 U.S.C. 154(b) by 656 days.

(21) Appl. No.: 10/362,561

(22) PCT Filed: Aug. 28, 2001

(86) PCT No.: PCT/FR01/02683

§ 371 (c)(1),
(2), (4) Date: Mar. 3, 2003

(87) PCT Pub. No.: WO02/20370

PCT Pub. Date: Mar. 14, 2002

(65) Prior Publication Data

US 2004/0000306 A1    Jan. 1, 2004

(30) Foreign Application Priority Data

Sep. 7, 2000    (FR) .................................. 00 11425

(51) Int. Cl.
*A61M 11/00* (2006.01)
*A61M 15/00* (2006.01)
*B65D 88/54* (2006.01)
*A62C 11/00* (2006.01)

(52) U.S. Cl. ........................... 128/200.14; 128/200.12; 128/200.22; 128/200.23; 128/203.12; 222/321.7; 239/333

(58) Field of Classification Search .......... 128/200.15, 128/200.14, 200.19, 200.22, 203.12, 205.16, 128/205.18; 222/321.8, 321.7, 402.13, 402.15, 222/402.1, 505; 239/333, 337, 340
See application file for complete search history.

(56) References Cited

U.S. PATENT DOCUMENTS

| | | | | | |
|---|---|---|---|---|---|
| 4,771,769 | A | * | 9/1988 | Hegemann et al. ..... | 128/200.22 |
| 5,570,821 | A | * | 11/1996 | DeJonge ..................... | 222/391 |
| 5,584,815 | A | * | 12/1996 | Pawelka et al. ............ | 604/191 |
| 6,007,515 | A | * | 12/1999 | Epstein et al. ................ | 604/82 |
| 6,033,384 | A | * | 3/2000 | Py .............................. | 604/186 |
| 6,599,272 | B1 | * | 7/2003 | Hjertman et al. ........... | 604/209 |
| 7,011,234 | B2 | * | 3/2006 | Stradella ..................... | 222/129 |
| 2005/0098175 | A1 | * | 5/2005 | Stradella ................ | 128/202.17 |
| 2005/0284890 | A1 | * | 12/2005 | Heldt et al. .............. | 222/321.7 |

\* cited by examiner

*Primary Examiner*—Justine R. Yu
*Assistant Examiner*—Amadeus Lopez
(74) *Attorney, Agent, or Firm*—Sughrue Mion, PLLC

(57) ABSTRACT

A fluid dispenser device including a body (1), a reservoir unit (3) having a reservoir containing one dose or two half-doses of fluid, a dispensing member mounted to move axially inside the reservoir (3) between a rest position and a dispensing position, and an actuating element (5) that is mounted to move between a rest position and an actuating position. The actuating element (5) is disposed laterally, and has an end portion provided with a cam surface (6) which co-operates with the dispensing member (8) or the reservoir unit (3), the actuating element (5) being moved in a direction that is different from, and in particular substantially perpendicular to, the axial direction in which the dispensing member (8) moves relative to the reservoir.

16 Claims, 2 Drawing Sheets

DEVICE FOR DISTRIBUTING A FLUID OF THE SINGLE DOSE OR HALF DOSE TYPE

This application claims priority from French Application No. 00/11425, filed Sep. 7, 2000.

FIELD OF THE INVENTION

The present invention relates to a fluid dispenser device, and more particularly to a fluid dispenser device of the one-dose or two-dose type, i.e. containing one dose or two half-doses of fluid to be dispensed.

BACKGROUND OF THE INVENTION

In the field of nasal spray devices of the one-dose or two-dose type, ergonomic and operating constraints and needs exist that are different from those that exist in multi-dose systems. In particular, this is due to the small size of the devices, which can give rise to handling difficulties. In addition, when the dispenser device is a two-dose device, the dose must be subdivided into two half-doses to be dispensed successively, one in each nostril. It is then essential to guarantee that the dose is subdivided safely and reliably.

Furthermore, one-dose or two-dose devices are often used to dispense medication that is designed to be taken once only, such as vaccines or medication to be taken in an emergency, and sometimes such devices are not designed for self-administration by the patient, but rather they are designed to be dispensed to the patient by another person. That makes it absolutely necessary for the nasal device to be positioned correctly in the nostril, and for it to be simple, safe, and reliable to operate.

Currently, no fully satisfactory solution has been proposed for simultaneously solving those safety and reliability problems. In order to subdivide the dose into two half-doses in a two-dose device for dispensing separately into each of the two nostrils, existing devices are generally made up of two elements, one of which supports the reservoir, the other element supporting the piston. When they are compressed axially towards each other, the first half-dose is delivered through the dispensing orifice into the nostril. In order to subdivide the dose, the stroke of the piston is stopped half-way along its length by a shoulder, and in order for the piston to travel over the second portion of its stroke, i.e. in order to dispense the second half-dose, it is necessary to turn the piston element manually relative to the reservoir. That type of system is safe and accurate, but it requires relatively complex handling, and thus both hands to be used in order to obtain the desired result and to be capable of dispensing the two half-doses successively in respectively ones of the two nostrils.

Other types of solution also include an abutment formed by a shoulder and turning, but turning is performed automatically by the system, e.g. by means of a resilient component such as a spring, as soon as the piston ceases to be pressed, after the first half-dose has been dispensed. That system is relatively simple to operate but it is not completely safe because the piston ceasing to be pressed can occur unintentionally, e.g. due to shaky hands, to indecisiveness, to fear of the spray entering the nose, etc. The result is that the two half-doses might be dispensed into the same nostril.

Concerning the ergonomic problem due to the small size of the device, existing devices propose no solution. Such devices need to be pressed axially towards the nostril, and that is relatively difficult to achieve because of the relatively small size of that type of device, the difficulty being even greater when the administration is performed by another person. The axial pressing required to actuate the device can cause the device to move into the nostril and give rise to injury, and even a risk of the dose being dispensed poorly because of a reaction by the patient, e.g. the patient recoiling suddenly as the dispensing is taking place. An object is thus to obtain a dispensing orifice which remains stationary throughout the dispensing of the dose into the nostril, which can be particularly important, in particular with medication to be taken once only, such as vaccines, for which inaccurate metering of the dose cannot be corrected by a second administration.

Document U.S. Pat. No. 5,570,821 discloses a semi-liquid fluid dispenser having a ratchet column associated with a piston, said ratchet column being displaced vertically by means of a lateral actuating button.

SUMMARY OF THE INVENTION

An object of the present invention is to provide a fluid dispenser device that does not reproduce the above-mentioned drawbacks.

In particular, an object of the present invention is to provide a fluid dispenser device that is inexpensive and easy to use, independently of its small size, even by another person.

Another object of the present invention is to provide a fluid dispenser device that subdivides the dose into two half-doses simply, safely, and reliably when it is a two-dose device, and that does not require both hands to be used to dispense the two half-doses into respective ones of the nostrils.

Another object of the present invention is to provide a fluid dispenser device that is simple and inexpensive to manufacture and to assemble.

To these ends, the present invention provides a fluid dispenser device comprising a body, a reservoir unit comprising a reservoir containing one dose or two half-doses of fluid, a dispensing member such as a piston mounted to move axially inside the reservoir between a rest position and a dispensing position, and an actuating element that is mounted to move between a rest position and an actuating position, said fluid dispenser device being characterized in that said actuating element is disposed laterally, and has an end portion provided with a cam surface which co-operates with said dispensing member or said reservoir unit, said actuating element being moved in a direction that is different from, and in particular substantially perpendicular to, the axial direction in which the dispensing member moves relative to the reservoir.

In a first variant embodiment, the actuating element is mounted to slide in said body and moves in translation.

In another variant embodiment, said lateral actuating element is mounted to pivot on said body, and moves in rotation about a pivot pin.

In a first embodiment of the invention, the reservoir contains a single dose of fluid, the dispensing member or the reservoir unit being provided with at least one projection co-operating with said cam surface of said actuating element.

In a second embodiment, the reservoir contains two half-doses of fluid, the device being provided with dose-splitting means.

Advantageously, the actuating element is provided with resilient return means which return it to its rest position after the first half-dose has been delivered, and the dose-splitting means are implemented such that the second half-dose is delivered when the actuating element is moved into its actuating position again.

Advantageously, the dispensing member or the reservoir unit is provided with at least two projections that are offset axially, at least a first projection co-operating with the cam surface to deliver the first half-dose, and at least a second projection co-operating with the cam surface for delivering the second half-dose.

Advantageously, said at least one second projection is provided on a resilient arm secured to or integral with the dispensing member or the reservoir unit, said arm moving out of the way when the actuating element co-operates with said at least one projection for delivering the first half-dose, and returning resiliently to its initial position when the actuating element is returned to its rest position by the resilient return means, after the first half-dose has been delivered, so that said at least one second projection co-operates with the cam surface of said actuating element when said actuating element is moved again into its actuating position for delivering the second half-dose.

Advantageously, said cam surface of the actuating element is a sloping surface transforming the substantially radial movement of the actuating element into an axial movement of the dispensing member or of the reservoir unit.

Advantageously, said actuating element is made integrally with said body, a bridge of flexible material forming the pivot pin.

In a first variant embodiment, the reservoir unit is fixed relative to said body, said actuating element co-operating with said dispensing member.

In a second variant embodiment, the dispensing member is fixed relative to said body, said actuating element co-operating with said reservoir unit.

BRIEF DESCRIPTION OF THE DRAWINGS

Other advantages and characteristics of the present invention will appear more clearly on reading the following detailed description of two embodiments of the invention, given with reference to the accompanying drawings which are given by way of non-limiting example, and in which.

DETAILED DESCRIPTION OF EXEMPLARY EMBODIMENTS OF THE INVENTION

Figure 1:
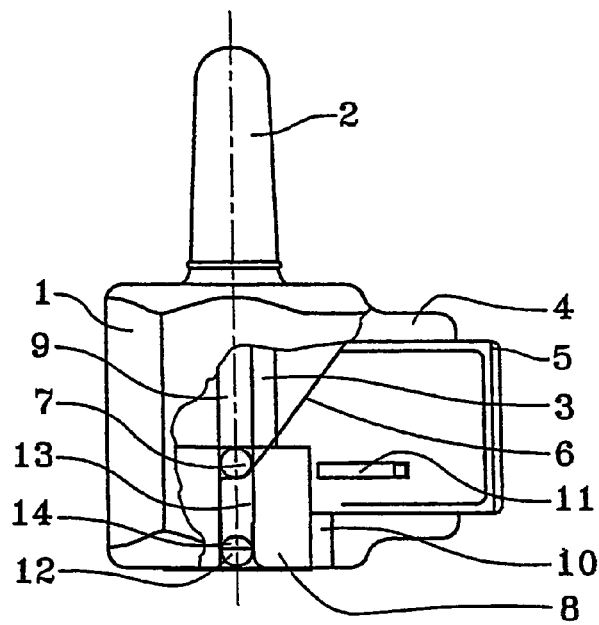
FIG. 1 is a diagrammatic section view of a first embodiment of a fluid dispenser device of the invention.
Figure 2:
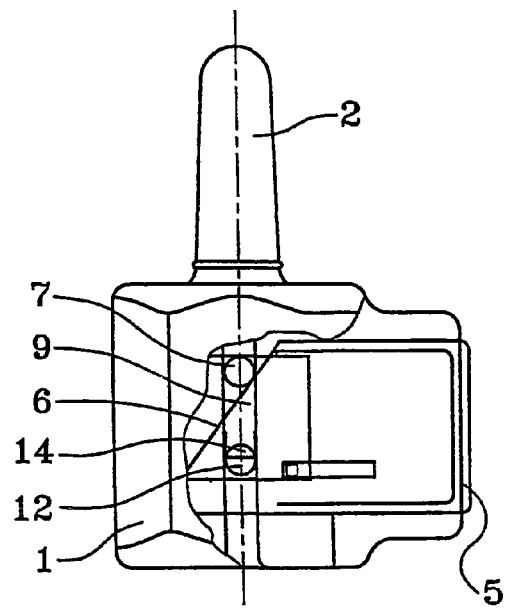
FIG. 2 is a view similar to the FIG. 1 view, after a first dose has been delivered.
Figure 3:
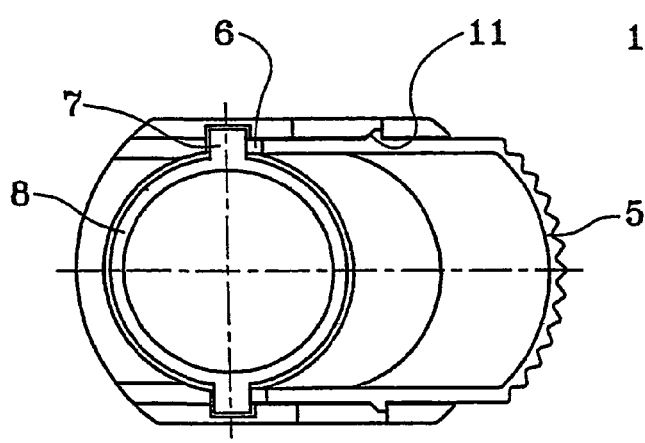
FIGS. 3 and 4 are diagrammatic horizontal section views, seen looking from above, of the device of FIGS. 1 and 2.
Figure 4:
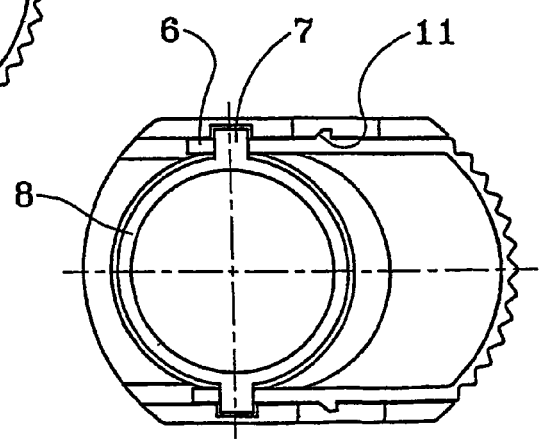

With reference to FIGS. 1 to 4, the device comprises a main body 1 which supports a nasal applicator 2 incorporating a dispensing orifice. A reservoir unit 3 comprising a reservoir containing one dose or two half-doses of fluid is fixed into said body 1. The body 1 is further provided with a hollow side sleeve 4 which slidably receives an actuating element 5 such as a push button. The actuating element 5 is provided with a cam surface 6, which is preferably implemented in the form of one or more sloping surfaces. A dispensing member 8, such as a piston, is slidably mounted inside the reservoir, and it moves between a rest position shown in FIG. 1 and a delivery position, the piston moving axially inside said reservoir. Advantageously, the cam surface 6 of the actuating element 5 (in particular made up of the sloping surfaces) co-operates with at least one and preferably two projections 7 which are formed on the piston element 8. The pair of projections 7 are inserted into and slidably received in respective ones of two grooves 9 which are formed in the wall of the cavity 10 of the body 1 in which the piston 8 slides while it is being actuated. The actuating element 5 may also be provided with retaining means 11 which prevent the actuating element from being removed accidentally from the body, and with resilient return means which are not shown in the drawings. In the embodiment shown in FIGS. 1 and 2, which show a two-dose device, the piston 8 is also provided with a second pair of projections 12, which are advantageously formed on two resilient arms 13 which are integral parts of the piston 8. The projections 12 are advantageously provided with thickened portions 14 going towards the top portion of the device.

The device shown in FIGS. 1 to 4 operates as follows. In order to dispense a first half-dose, the actuating element 5 is pushed in a direction that is substantially perpendicular to the axial direction, and the sloping surfaces 6 co-operate with the pair of projections 7 to urge the piston 8 axially, thereby causing it to slide upwards and to deliver the fluid. During this action, the second pair of projections 12 reach the bottom face of the actuating element 5, at the cam surface 6, and, by means of the thickened potions 14 and of the flexible arms 13, the projections 12 slide under the actuating element 5 until they reach the position shown in FIG. 2, which corresponds to the end of dispensing of the first half-dose. Whereupon, when the actuating element 5 ceases to be pressed, it returns to its rest position by means of resilient return means (not shown). While this is taking place, the second pair of projections 12 are released, and the resilient arms can return, by their resilience, to their initial positions in which the projections 12 are situated in the same positions as the pair of projections 7 prior to delivery of the first half-dose. The device is then ready to dispense the second half-dose, which is achieved by pressing radially again on the actuating element 5. The advantage of the device is clear, namely that it is not necessary to turn the actuating element 5 at all between delivery of the two half-doses. Therefore, the two half-doses can be dispensed successively into respective ones of the two nostrils by using one hand only.

However, the invention is not limited to a device of the two-dose type, and it is also applicable to devices of the one-dose type, in which a single dose is to be delivered. In which case, the device operates similarly to the mode of operation described above, except that only one pair of projections 7 are provided on the piston, since the projections 12 and the arms 13 are then unnecessary, as are the resilient return means.

Figure 5:
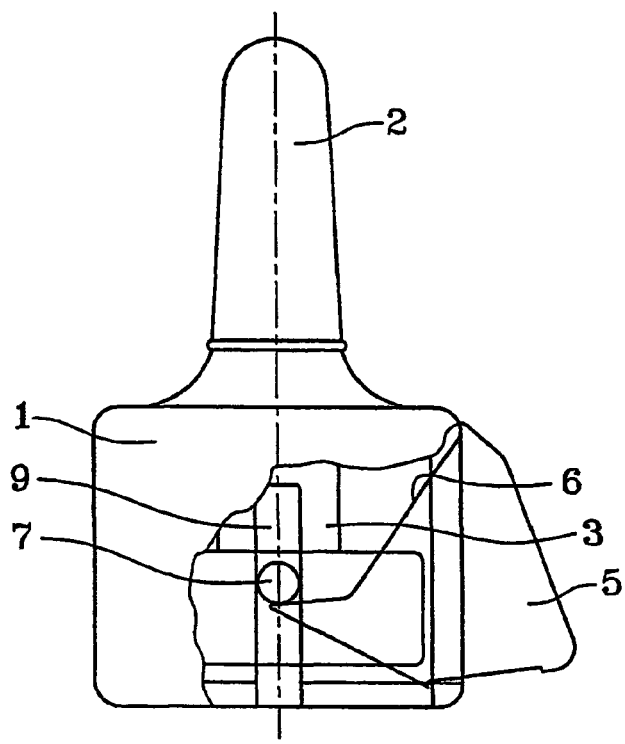
FIG. 5 is a diagrammatic view of a second embodiment of the invention, in the rest position.
Figure 6:
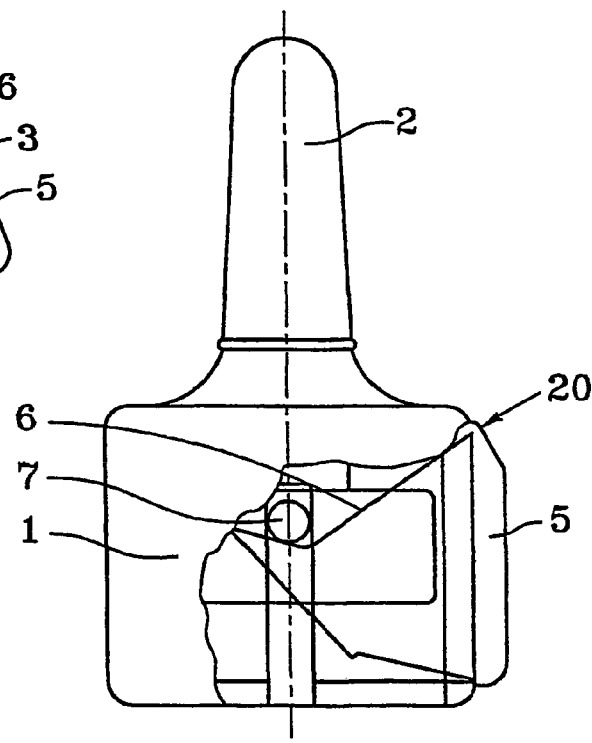
FIG. 6 is a view similar to the FIG. 5 view, after a dose has been delivered.
Figure 7:
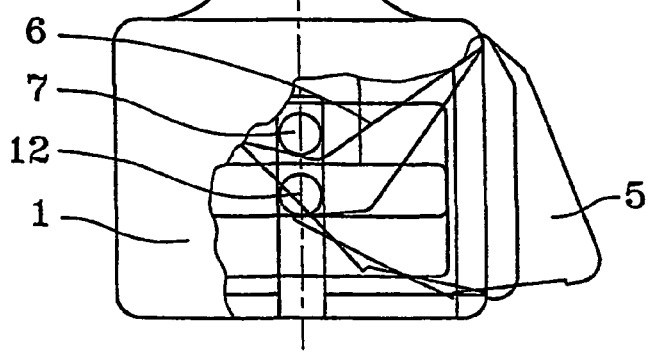
FIG. 7 is a view similar to the views of FIGS. 5 and 6, showing an embodiment of the two-dose type.

FIGS. 5 to 7 show a second embodiment of the invention, in which the actuating element 5 is not mounted to slide inside the body 1, but rather it is mounted to pivot on said body 1. The device operates relatively similarly to the mode of operation described above, the shape of the cam surface 6 naturally being adapted to match the turning movement effected by the actuating element 5. FIGS. 5 and 6 show clearly the rest position and the actuating position for a device of the one-dose type.

FIG. 7 shows the above embodiment for a device of the two-dose type, which operates similarly to the above-described mode of operation, i.e. a second pair projections 12 are provided on the piston 8, said projections moving out of the way when the actuating element 5 is actuated to deliver the first half-dose, and then returning to the position corresponding to the first projections 7 being in the initial position, for delivering the second half-dose.

Advantageously, as shown in FIGS. 5 to 7, the actuating element is made integrally with the body 1, and is connected thereto by a bridge of material which forms the pivot pin 20.

Advantageously, energy accumulation means may be provided on the actuating element 5 or on the body 1, e.g. in the form of a lug or the like. The angle of inclination of the sloping surface 6 may also be determined such as to increase the force exerted by the actuating element on piston or the reservoir.

In a variant to the above-described embodiments, the lateral actuating element may also co-operate with the reservoir unit. In which case, said reservoir unit incorporates the first and/or second projections. It is then the piston that is fixed relative to the body of the device, and the reservoir that is moved axially by the lateral actuating element.

The invention therefore makes it possible to obtain a device of the two-dose or of the one-dose type that enables the fluid to be dispensed into the nostril while keeping the device stationary axially inside the nostril at the time of delivery of the fluid, no axial force being generated on the device at that time. Thus, the device is very easy for another person to actuate since there is no risk of them injuring the patient. Finally, the device can be actuated with a single hand, which is a very important advantage, while also guaranteeing that it operates safely and reliably each time it is actuated.

The invention claimed is:

1. A fluid spray dispenser device comprising a body (1), a nasal applicator (2) adapted to be inserted into a nostril, a reservoir unit (3) comprising a reservoir containing only one single dose or only two half-doses of fluid to be sprayed in a nostril through the nasal applicator, a dispensing member (8) mounted to move axially inside the reservoir (3) between a rest position and a dispensing position, and an actuating element (5) that is mounted to move between a rest position and an actuating position, said fluid dispenser device being characterized in that said actuating element (5) is disposed laterally, and has an end portion provided with a cam surface (6) which co-operates with said dispensing member (8) or said reservoir unit (3), said actuating element (5) being moved in a direction that is different from, and in particular substantially perpendicular to, the axial direction in which the dispensing member (8) moves relative to the reservoir.

2. A device according to claim 1, in which the lateral actuating element (5) is mounted to slide in said body (1) and moves in translation.

3. A device according to claim 1, in which said lateral actuating element (5) is mounted to pivot on said body (1), and moves in rotation about a pivot pin (20).

4. A device according to claim 3, in which said actuating element (5) is made integrally with said body (1), a bridge of flexible material (20) forming the pivot pin.

5. A device according to claim 1, in which the reservoir contains a single dose of fluid, the dispensing member (8) or the reservoir unit (3) being provided with at least one projection (7) co-operating with said cam surface (6) of said actuating element (5).

6. A device according to claim 1, in which the reservoir (3) contains two half-doses of fluid, the device being provided with dose-splitting means.

7. A device according to claim 6, in which the actuating element (5) is provided with resilient return means which return it to its rest position after the first half-dose has been delivered, and the dose-splitting means are implemented such that the second half-dose is delivered when the actuating element (5) is moved into its actuating position again.

8. A device according to claim 6, in which the dispensing member (8) or the reservoir unit (3) is provided with at least two projections (7,12) that are offset axially, at least a first projection (7) co-operating with the cam surface (6) to deliver the first half-dose, and at least a second projection (12) co-operating with the cam surface (6) for delivering the second half-dose.

9. A device according to claim 8, in which said at least one second projection (12) is provided on a resilient arm (13) secured to or integral with the dispensing member (8) or the reservoir unit (3), said arm (13) moving out of the way when the actuating element (5) co-operates with said at least one projection (7) for delivering the first half-dose, and returning resiliently to its initial position when the actuating element (5) is returned to its rest position by the resilient return means, after the first half-dose has been delivered, so that said at least one second projection (12) co-operates with the cam surface (6) of said actuating element (5) when said actuating element is moved again into its actuating position for delivering the second half-dose.

10. A device according to claim 1, in which said cam surface (6) of the actuating element (5) is a sloping surface transforming the substantially radial movement of the actuating element (5) into an axial movement of the dispensing member (8) or of the reservoir unit (3).

11. A device according to claim 1, in which the reservoir unit (3) is fixed relative to said body (1), said actuating element (5) co-operating with said dispensing member (8).

12. A device according to claim 1, in which the dispensing member (8) is fixed relative to said body (1), said actuating element (5) co-operating with said reservoir unit (3).

13. The device according to claim 1, wherein the dispensing member comprises a piston.

14. A fluid spray dispenser device comprising:
a body;
a nasal applicator adapted to be inserted into a nostril;
a reservoir comprising a single dose or two half-doses of fluid medication designed to be administered by spraying in a nostril through the nasal applicator;
a dispensing member mounted to move axially inside the reservoir between a rest position and a dispensing position; and
an actuating element mounted to move between a rest position and an actuating position; and
wherein the actuating element projects laterally and comprises an end portion comprising a cam surface that co-operates with the dispensing member or the reservoir unit, the actuating element moveable in a direction transverse to the axial direction in which the dispensing member moves relative to the reservoir.

15. The device according to claim 14, wherein the dispensing member is fixed relative to the body and the actuating element co-operates with the reservoir.

16. A fluid dispenser device comprising a body (1), a reservoir unit (3) comprising a reservoir containing one dose or two half-doses of fluid, a dispensing member mounted to move axially inside the reservoir (3) between a rest position and a dispensing position, and an actuating element (5) that is mounted to move between a rest position and an actuating position, said fluid dispenser device being characterized in that said actuating element (5) is disposed laterally, and has an end portion provided with a cam surface (6) which co-operates with said dispensing member (8) or said reservoir unit (3), said actuating element (5) being moved in a direction that is different from, and in particular substantially perpendicular to, the axial direction in which the dispensing member (8) moves relative to the reservoir; and wherein the dispensing member (8) is fixed relative to said body (1), said actuating element (5) co-operating with said reservoir unit (3).

* * * * *